US007922679B1

(12) United States Patent
Chapman et al.

(10) Patent No.: US 7,922,679 B1
(45) Date of Patent: Apr. 12, 2011

(54) BLOOD-DRAW FINGER RESTRAINT

(76) Inventors: Angelina Maria Chapman, Suisun City, CA (US); Daniel Thomas Chapman, Suisun City, CA (US)

( * ) Notice: Subject to any disclaimer, the term of this patent is extended or adjusted under 35 U.S.C. 154(b) by 0 days.

(21) Appl. No.: 11/507,722

(22) Filed: Aug. 21, 2006

(51) Int. Cl.
 *A61F 5/00* (2006.01)
(52) U.S. Cl. ............................................. 602/20; 602/22
(58) Field of Classification Search ............... 602/20–22; 128/880; 2/21; 127/880
 See application file for complete search history.

(56) References Cited

U.S. PATENT DOCUMENTS

| 1,306,442 | A | * | 6/1919 | Sansotta | 2/21 |
| 2,548,378 | A | * | 4/1951 | Kleinfeld | 602/22 |
| 4,194,736 | A | * | 3/1980 | Loafman | 473/4 |
| 5,517,692 | A | * | 5/1996 | Wunderlich-Kehm | 2/21 |
| 5,613,938 | A | * | 3/1997 | Kaiser et al. | 600/201 |
| 5,925,008 | A | * | 7/1999 | Douglas | 602/22 |
| 6,575,925 | B1 | * | 6/2003 | Noble | 602/20 |
| 2004/0144389 | A1 | * | 7/2004 | Berrehail | 128/846 |
| 2006/0069334 | A1 | * | 3/2006 | Moskowitz | 602/5 |

\* cited by examiner

*Primary Examiner* — Michael A. Brown
(74) *Attorney, Agent, or Firm* — Risto A. Rinne, Jr.

(57) ABSTRACT

An apparatus for drawing blood from a finger includes a flexible band, at least a portion of which is adapted to surround a portion of a finger. A remaining portion of the apparatus is disposed under at least one joint of the finger. The apparatus provides sufficient strength along its longitudinal length to restrict a child or other person from excessively bending the joint when the finger restraint is in position. After a puncture is provided near the tip of the finger, the apparatus is then squeezed to help force an additional quantity of blood to flow out through the puncture. After the blood sample is taken, the apparatus continues to "restrain" the finger until a required bandage is applied. A few of the many possible modifications are also shown.

8 Claims, 2 Drawing Sheets

BLOOD-DRAW FINGER RESTRAINT

BACKGROUND OF THE INVENTION

1. Field of the Invention

The present invention, in general, relates to drawing blood and, more particularly, to drawing blood from children.

No one likes to have blood drawn from their body for use in testing. The skin must be pierced to access human blood, and pain is an inherent side effect arising whenever the skin is punctured or otherwise penetrated.

Adults understand the necessity of such a procedure and its potential for benefit and, therefore, make an attempt to endure the discomfort. Nevertheless, many adults find the experience quite uncomfortable, even so.

However, for children, any attempt to draw blood can be especially difficult to accomplish. For most blood-draw procedures involving younger children, a finger is pricked and then squeezed to force a sufficient quantity of blood to the surface for capture and testing.

While this method is generally preferred for several reasons over the procedures that are used with adults, it is often still a traumatic experience for most children.

Their reactions are governed by instinctual responses to the experiences they are having. When a finger is punctured, the resultant pain causes the child to tighten their fingers in a fist. This is instinctual, and it happens virtually all of the time.

A lab assistant, medical assistant, phlebotomist, nurse, LVN, medical student or intern, lab technician (lab technician is generally used hereinafter to refer to any person that is drawing blood), or any other person who is drawing the blood must then force the fist open, in particular, the finger that has been punctured. The child is using all of his or her strength to prevent this from happening.

The ensuing struggle heightens the drama of the moment. The child may be crying or screaming in protest as the lab technician attempts to force open the hand.

The squeezing of the fist by the child combined with the pressure exerted by the lab technician is likely to force additional blood out from the puncture that was made. This blood is likely to be smeared on the hands of both child and lab technician, rather than available for collection.

The visible blood adds even more trauma and drama to the moment which makes the child want to close his or her hand all the more.

After the lab technician has forced open the punctured digit, the lab technician must then apply additional pressure to the digit (finger) to express therefrom the required amount of blood for the test.

This act is also painful, and the child will again attempt to close his or her hand.

The lab technician must then apply the expressed blood to whatever test device is being used or otherwise collect it. This is profoundly difficult to do because the child is constantly crying, screaming, attempting to jerk the hand away from the lab technician, and most of all forcibly attempting to make a fist and deny access to the punctured finger.

The blood-draw procedure for children is especially difficult, and many are the lab technicians who avoid doing so or admit of their own inadequacy at drawing blood from children. The few who seem to prevail more often than not at the task are generally regarded as "wonder workers" by their peers. These peers are only too happy to give the title to someone else because perhaps, a primary intention of theirs is actually to delegate the task itself to the "wonder worker."

It is apparent that the child, at times, is traumatized by the procedure of drawing blood.

When a lab technician is unsuccessful, that technician finds someone else to assist in drawing the blood. The lab technician assigned to draw blood usually does the job, but they call for assistance from co-workers to assist with holding the child's hand to gain access to the fingers to finish the procedure.

In addition to the emotional factors involved, the process of extracting blood (i.e., doing a blood-draw) from a child is almost always quite time-consuming.

It takes time to open the finger after the child forces it closed. It takes time to quiet and calm the child and to express the blood.

Also, if the attempt fails and must be repeated, that adds considerably to the time involved. This makes the drawing of blood from children costly because of the cost of labor. That cost is proportional to the time required, and a lot of time is required when drawing blood from children.

Furthermore, when repeated attempts are required, additional sterilized lancets (to puncture the finger) and sterilizing swabs are also required. This increases the cost of the equipment that is used, as well.

Because of the challenges as mentioned above, only highly-skilled lab technicians are able to draw blood from children.

Also, as mentioned above, it is typically necessary to squeeze the finger to express (i.e., to force) a sufficient quantity of blood from the puncture (lancing) that was made.

This, too, is somewhat traumatic for the child. They do not like the localized pressure of the lab technician squeezing their finger because this action increases the discomfort (pain) that the child is experiencing.

The step of squeezing the finger to express a quantity of blood therefrom is also fraught with difficulty.

Usually, a single lab-technician cannot simultaneously do it all when drawing blood from children. He (or she) cannot hold the finger open against the resistance and jerking by the child, lance it, squeeze it to express blood from the puncture, apply a test strip to the blood or otherwise collect the blood, and then bandage the puncture. Therefore, the additional services of an assistant (or the wonder worker) are usually also required by the lab-technician. This essentially doubles the required amount of labor which substantially increases the cost of drawing blood from children.

Accordingly, there exists today a need for a blood-draw finger restraint that helps ameliorate the above-mentioned problems and difficulties.

Clearly, such an apparatus would be a useful, cost-effective and desirable device.

2. Description of Prior Art

In general, various types of blood drawing apparatus are known. While the structural arrangements of the above described and known devices may have, at first appearance, certain similarities with the present invention, they differ in material respects. These differences, which will be described in more detail hereinafter, are essential for the effective use of the invention and which admit of the advantages that are not available with the prior devices.

OBJECTS AND SUMMARY OF THE INVENTION

It is an object of the present invention to provide a blood-draw finger restraint that helps prevent a child from contracting a finger from which blood is being drawn.

It is also an important object of the invention to provide a blood-draw finger restraint that helps prevent a child from contracting a finger that has been punctured for drawing blood.

Another object of the invention is to provide a blood-draw finger restraint that helps retain a finger in an open position during a blood-draw procedure.

Still another object of the invention is to provide a blood-draw finger restraint that is inexpensive to manufacture.

Still yet another object of the invention is to provide a blood-draw finger restraint that is disposable.

Yet another important object of the invention is to provide a blood-draw finger restraint that is sterile.

Still yet another important object of the invention is to provide a blood-draw finger restraint that makes it easier to extract blood from a finger.

A first continuing object of the invention is to provide a blood-draw finger restraint that makes it easier to access extracted blood with a test strip or other type of collection device.

A second continuing object of the invention is to provide a blood-draw finger restraint that is adjustable to fit different size fingers.

A third continuing object of the invention is to provide a blood-draw finger restraint that can include an ornament design useful in distracting or amusing a child.

A fourth continuing object of the invention is to provide a blood-draw finger restraint that prevents at least one joint of at least one finger from flexing or bending an excessive amount during a blood-draw procedure.

A fifth continuing object of the invention is to provide a blood-draw finger restraint that can also be provided in a variety of sizes to better fit different size fingers.

A sixth continuing object of the invention is to provide a blood-draw finger restraint that is adapted to fit over a portion of a finger sufficient to prevent at least one joint from flexing an excessive amount.

A seventh continuing object of the invention is to provide a blood-draw finger restraint that includes a flexible band that is adapted to fit over a portion of a finger and wherein the finger restraint is able to prevent at least one joint from flexing an excessive amount.

An eighth continuing object of the invention is to provide a blood-draw finger restraint that includes a flexible band that is adapted to fit over a portion of a finger and wherein the flexible band is adapted to be squeezed to help express blood from a puncture that is provided through the skin of the finger.

A ninth continuing object of the invention is to provide a blood-draw finger restraint that allows a lab technician to better maintain control of a finger during a blood draw procedure.

A tenth continuing object of the invention is to provide a blood-draw finger restraint that helps prevent contamination of blood from occurring during a blood-draw procedure.

An eleventh continuing object of the invention is to provide a blood-draw finger restraint that prevents a premature expression of blood through a puncture from occurring during a blood-draw procedure.

A twelfth continuing object of the invention is to provide a blood-draw finger restraint that helps maintain access to a tip of a finger for a required bandage application over a puncture that is made in the tip.

A thirteenth continuing object of the invention is to provide a blood-draw finger restraint that helps to make it easier to draw blood from people that are between about nine months to about six years of age.

A fourteenth continuing object of the invention is to provide a blood-draw finger restraint that provides access to a tip of a finger for lancing (puncturing). and for the expression of blood therefrom.

A fifteenth continuing object of the invention is to provide a blood-draw finger restraint that provides access to a tip of a finger for the expression of blood therefrom.

A sixteenth continuing object of the invention is to provide a blood-draw finger restraint that provides access to a tip of a finger for the application of a test strip to a quantity of blood that is disposed on the tip of the finger.

A sixteenth continuing object of the invention is to provide a blood-draw finger restraint that provides access to a tip of a finger for the collection of a quantity of blood that is disposed on the tip of the finger.

A seventeenth continuing object of the invention is to provide a blood-draw finger restraint that allows blood draw from children to be accomplished by a singular person whereas before, two people were typically required.

Briefly, a blood-draw finger restraint that is constructed in accordance with the principles of the present invention has a flexible band, at least a portion of which is adapted to surround a portion of a finger of a child. A remaining portion of the blood-draw finger restraint is disposed under at least one joint of the finger. The finger restraint provides sufficient strength along its length to restrict a child from excessively bending the joint of the finger when the finger restraint is in position. The flexible band or other portion of the blood-draw finger restraint is then squeezed to help force an additional quantity of blood to flow out of a puncture that is provided through the skin of the finger. Several possible modifications are also shown and briefly discussed.

DETAILED DESCRIPTION OF THE INVENTION

Figure 1:
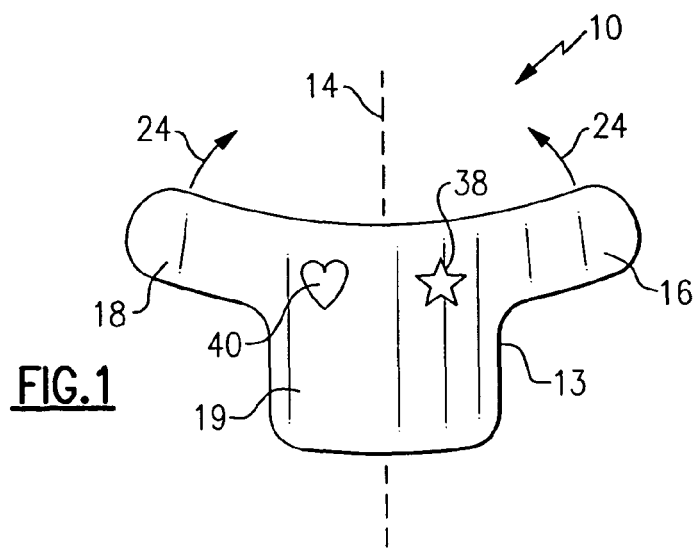
FIG. 1 is a plan view of a blood-draw finger restraint.
Figure 2:
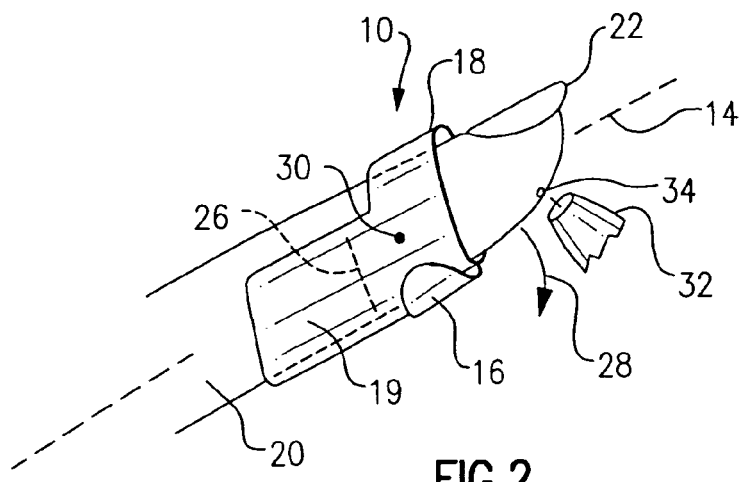
FIG. 2 is a side view of the blood-draw finger restraint of FIG. 1 disposed over a finger of a child.
Figure 3:
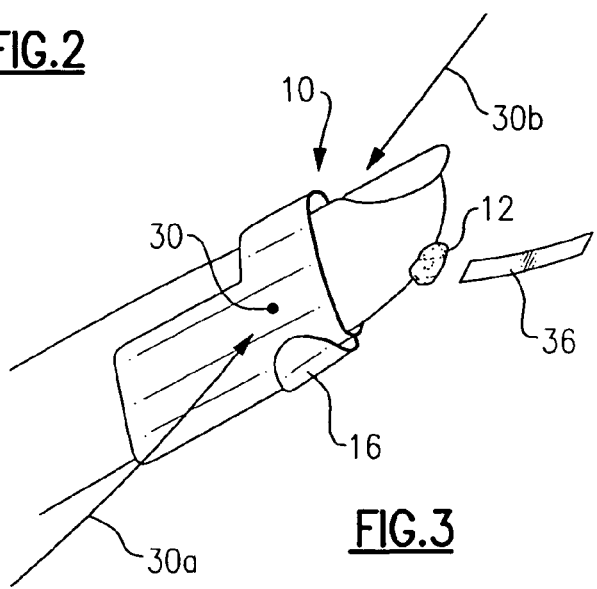
FIG. 3 is a side view of the blood-draw finger restraint of FIG. 2 being squeezed to help express blood through an opening that is provided in the finger.
Figure 4A:
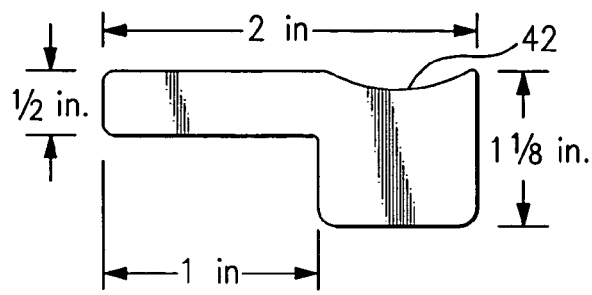
FIG. 4 is top view of a few possible alternate shapes of the finger restraint.
Figure 4B:
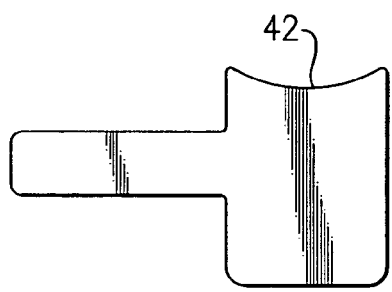
Figure 4C:
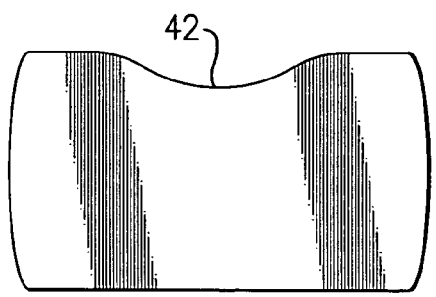
Figure 4D:
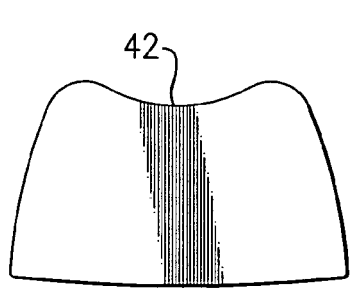
Figure 4E:
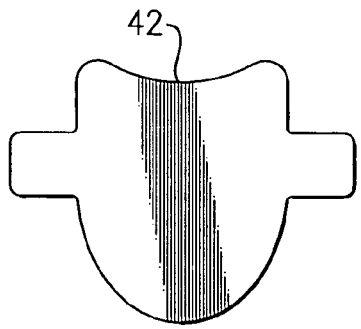

Referring on occasion to FIGS. 1-3 is shown, a blood-draw finger restraint, identified in general by the reference numeral 10.

As used herein the term "finger" is intended to include any digit of either hand, including the thumb. The blood-draw finger restraint 10 is primarily intended for use during the drawing of blood 12 (FIG. 3) from a child or toddler ranging from about nine months of age to about six years of age. While it can be used with people of other ages, the benefits derived by the instant invention are generally greatest when used with people that fall within the above-specified age group. As used herein, the term "children" is intended to include all persons within the above specified age group, including toddlers.

Its use is preferred when attempting to draw blood from children because of the tendency a child has to form a fist during the procedure. However, the blood-draw finger restraint 10 can, of course, be provided in any desired size for use with people of any age.

After having had benefit of the instant disclosure, numerous possible modifications and variations will become apparent to those having ordinary skill in the art that can be made to the blood-draw finger restraint 10. These modifications and variations include changes regarding the material used to form the blood-draw finger restraint 10 as well as changes made regarding its shape and structure.

For the purpose of this disclosure a preferred material for the blood-draw finger restraint 10 includes a sheet 13 of plastic that is flexible about a longitudinal axis 14 (dashed lines, FIG. 1). It is preferred because it can be manufactured at extremely low cost and provided for singular use and disposal.

The sheet 13 includes a first protruding band 16 and a second protruding band 18 that are disposed on one side of the sheet 13 and on opposite ends of the sheet 13. The first and second protruding bands 16, 18 are formed integral with respect to the material used to form the remainder of the sheet 13.

A remainder of the sheet 13 includes a main body portion 19 that is also preferably formed as an integral part thereof.

When the sheet 13 is disposed as shown in FIG. 1, it is substantially planar. If desired, the sheet 13 can be shipped as shown in FIG. 1.

The sheet 13 is preferably provided in a disposable container (not shown) for opening prior to drawing blood from a finger 20 of the child. A quantity of the sheets 13 (or the blood-draw finger restraints 10) can be packaged together, as desired. Each of the blood-draw finger restraints 10 is preferably sterilized to preclude it from being a contributory cause of possible infection. The blood-draw finger restraint 10, as mentioned above, is intended for opening, use, and safe discard after use. It is not intended to be reused.

During use, the main body portion 19 is placed under and against the finger 20, on a side of the finger 20 that is opposite that of a nail 22 by a lab technician, medical-assistant, phlebotomist, nurse, LVN, student, intern, lab technician, doctor, or any other person who is drawing the blood.

The first protruding band 16 and the second protruding band 18 are each urged in the direction shown by arrows 24 until they are wrapped around the finger 20. The longitudinal axis 14 then passes through the center of the finger 20.

As the first protruding band 16 and the second protruding band 18 are each urged around the finger 20, the main body portion 19 also curves to match the shape of the finger 20.

When the blood-draw finger restraint 10 is disposed around the finger 20, as shown in FIG. 2, it is desirable that the first protruding band 16 and the second protruding band 18 have a combined length, including the length of the main body portion 19 that is disposed between the first and second protruding bands 16, 18, that is greater than the circumference of the finger 20 at the location of the finger where they are placed.

This causes at least some overlap by either the first protruding band 16 over the second protruding band 18 or by the second protruding band 18 over the first protruding band 16 and, depending on the size of the blood-draw finger restraint 10 and the circumference of the finger 20, possibly some overlap by either of the first or second protruding bands 16, 18 that may extend over a small section of the main body portion 19.

The overlap helps ensure that the blood-draw finger restraint 10 will be retained in position over the finger 20 during the blood-draw procedure.

Preferably, the blood-draw finger restraint 10 is not shipped flat but is preformed to include a natural tendency to curve around the longitudinal axis 14 and take the shape as shown in FIG. 2. This further helps to ensure that the blood-draw finger restraint 10 will remain in position over the finger 20.

The curvature of the first and second protruding bands 16, 18 and by the main body portion 19 provide an important benefit in that the blood-draw finger restraint 10 becomes significantly more rigid and resistant to flexing itself along the longitudinal axis 14 after it has taken a curved shape.

The material used to form the blood-draw finger restraint 10 is typically thin plastic, similar in thickness to the plastic that is commonly used to form the sidewalls of a plastic gallon milk container, as is commonly sold.

When this thin plastic is disposed on a flat plane, as shown in FIG. 1, it can readily be bent (i.e., curved) in any direction. Of course, if the blood-draw finger restraint 10 includes a preset (i.e. a pre-formed or built-in) tendency to curve as shown in FIG. 2, it will be difficult to curve it in any direction other than as shown. That is an added benefit of including the preset curvature into the blood-draw finger restraint 10 during manufacture. However, absent that tendency it would not take much force to flex or curve it along any possible axis passing there-through.

It is important to understand that once the blood-draw finger restraint 10 has either been forced into the position as shown in FIG. 2 or has readily adapted to that position because of its natural "built-in" preset tendency to curve in that direction as part of the manufacturing process, it will resist flexing (i.e., bending or curving) along any axis other than along the longitudinal axis 14.

Accordingly, the thin material that the blood-draw finger restraint 10 is made of becomes much stronger and much more resistant to bending (flexing) in other directions.

The blood-draw finger restraint 10, when placed over the finger 20, is typically placed near the tip of the finger 20, just behind the nail 22, as shown. This position covers an end joint 26 (dashed line) of the finger 20.

Accordingly, were it not for the restraint provided by the blood-draw finger restraint 10, the child would be able to flex a tip of their finger 20 (i.e., that portion of the finger 20 that is disposed between the end joint 26 and the furthermost portion of the nail 22) in a direction shown by arrow 28.

When the blood-draw finger restraint 10 is disposed as shown, it limits the ability of the finger 20 to bend about the end joint 26 in the direction of arrow 28. A small amount of bending is acceptable as it will not impede the blood-draw procedure. As mentioned above, the thin material used provides substantial resistance to any flexing of the finger 20 in the direction as shown by arrow 28.

A lab technician (not shown) that is drawing the blood from the child or infant, places the blood-draw finger restraint 10 around the finger 20, as shown. The lab technician then places typically either a tip of their thumb (not shown) or a tip of their forefinger (not shown) on a location identified by a spot 30. Typically, the spot 30 is not shown or otherwise included with the blood-draw finger restraint 10. It is shown only to assist in providing a better understanding of the use of the blood-draw finger restraint 10.

The lab technician would then simultaneously place the remaining tip of either their thumb or forefinger (whichever was not placed over the spot 30) on the opposite side of the blood-draw finger restraint 10 that is diametrically opposed to the location of the spot 30.

The position allows the lab technician to easily take control of the finger 20.

By placing the blood-draw finger restraint 10 in the position as shown, it also conveniently leaves the bottom of the tip of the finger 20 available (i.e., open and accessible) for puncturing with a lancet 32.

Different versions of the lancet 32 as are commonly used for this purpose are well known and are, therefore, not discussed herein. Use of the lancet 32 provides a puncture 34 (i.e., an opening) through the skin. The act of puncturing the skin is painful and the child will instinctively react to a "lancing" of their finger 20 by attempting to bend the finger 20 around the end joint 26 as shown in the direction of arrow 28.

The child would also likely react by attempting to bend all of the remaining joints (not shown) of the finger 20 also in the general direction as shown by arrow 28. Furthermore, the child would also likely react by similarly bending all of the remaining fingers (not shown) of the hand in the general direction as shown by arrow 28, thereby attempting to make a fist.

However, use of the blood-draw finger restraint 10 prevents this from happening with the finger 20. The lab technician, by holding the blood-draw finger restraint 10 as described hereinabove, is able to retain the finger 20 in the position, as shown, after use of the lancet 32 has created the puncture 34.

After creation of the puncture 34, the lab technician retains their grip and control of the finger 20 by continuing to apply a sufficient amount of force on the spot 30 and also to a diametrically opposed side of the blood-draw finger restraint 10. This level of force prevents bending of the finger 20.

It is normal for a small amount of blood 12 to flow out of the puncture 34; however, that amount is generally insufficient to adequately saturate a test strip 36 that is applied thereto. In lieu of the test strip 36, other test devices (not shown) or blood collection devices may be used.

However, it is important that the blood 12 be present in sufficient volume on the tip of the finger 20. According to the prior art approach to drawing blood from children, the lab technician would typically have to pry open the clenched finger 20 in order to gain access to the puncture. Then the lab technician would have to change his or her grip and attempt to squeeze the tip of the finger 20 in order to express (i.e., force) a sufficient quantity of the blood 12 to flow through the puncture 34.

Not only is this traumatic for the child, but it is also time consuming. An additional negative consequence from this prior approach is that during the process of prying open the finger and expressing the blood 12, the lab technician may inadvertently make contact with the blood 12 and possibly contaminate it.

Accordingly, the lab test data results may be inaccurate or inconclusive. Also, the blood 12 may be smeared and contact the skin and clothes of the child or of the lab technician or both, which is undesirable.

Because the lab technician must apply additional force to the finger 20 in order to pry it open, this very act may cause the finger 20 to express additional blood 12 through the puncture 34 at a time that is not desirable because the lab technician is not at that time prepared to contact the blood 12 with the test strip 36.

The blood 12 that is prematurely expressed while prying open the finger 20 is apt to smear. If smeared, the untimely expressed blood 12 removes a quantity of available blood 12 from the tip of the finger 20 which also makes it more difficult to later express an additional amount of blood 12, when needed.

These problems are eliminated by use of the blood-draw finger restraint 10. Use of the blood-draw finger restraint 10 retains the finger 20 substantially as shown, in an extended (i.e., straight) attitude.

As mentioned above after use of the lancet 32, the lab technician retains their grip and control of the finger 20 by continuing to apply a sufficient amount of force on the spot 30 and also to a diametrically opposed side of the blood-draw finger restraint 10.

To express the needed quantity of the blood 12 from the puncture 34, the lab technician does not change their hand position with respect to the finger 20. Instead, the lab technician merely increases the amount of force that he or she is applying to the spot 30 and the opposite side of the blood-draw finger restraint 10 as shown by arrows 30*a* and 30*b*, both of which point toward each other.

This increase of pressure causes the first and second protruding bands 16, 18 and the main body portion 19 of the blood-draw finger restraint 10 to flex an additional amount and to transfer a portion of the increased pressure to that portion of the finger 20 that is disposed underneath.

This automatically increases pressure within the tip of the finger 20 and expresses the additional required amount of blood 12 through the puncture.

Accordingly, no change in hand or finger position by the lab technician is required to express the blood 12. The lab technician can immediately increase pressure sufficient to express the blood 12 as soon as the puncture 34 is created. The child may not even be aware of the increased pressure. Perhaps even before the child knows it, the puncture 34 is provided and a sufficient quantity of blood 12 has been expressed (forced) through the puncture 34. The lab technician then applies the test strip 36 to the blood 12 and the procedure is over. Trauma is virtually eliminated. Time is saved. Stress is reduced.

Obviously, if additional test strips (not shown) must be used, they are applied in sequence. If an additional quantity of blood 12 is required to satisfy the demands of the additional test strips, the lab technician again increases pressure, as was described above, to express an additional quantity of the blood 12. The entire blood-draw procedure is completed in a smooth continuum in an absolute minimum amount of time.

The time required for the blood-draw procedure is greatly reduced by eliminating the steps of the lab technician having to pry open the clenched finger 20 after lancing and of having to change their grip upon the finger 20 in order to express the blood 12.

To help distract the child during the blood-draw procedure, any of a variety of ornamental shapes 38, 40 can be printed or embossed or otherwise included with the blood-draw finger restraint 10. The lab technician could conceivably distract the child just prior to lancing by asking them to look at or comment on the ornamental shapes 38, 40.

It is desirable also to ensure that the blood-draw finger restraint 10 includes rounded corners and edges that are not sharp. This is to help reduce the likelihood that a cut to the finger 20 can occur during the blood-draw procedure.

Many modifications are possible to the blood-draw finger restraint 10 after having had benefit of the instant disclosure. For example, if desired, the main body portion 19 could be modified to extend further in a direction away from the nail 22 and to cover more of the remaining joints of the finger 20. This could be of additional benefit in preventing the child from bending the finger 20 in the direction as shown by arrow 28.

Referring now to FIG. 4, a few possible alternate device shapes (4*a*-4*e*) of the finger restraint are shown, each example that is shown being in a plan view with the alternate shape disposed in a plane.

The dimensions of 4*a* are included to provide a preferred overall size that is sufficient for this particular modification to fit the greater variety of sizes of the finger 20, as is likely to be found on children. These dimensions also provide a general indication of possible dimensions for all possible versions of the blood-draw finger restraint 10. Of course, other sizes are possible to optimally accommodate other sizes of the finger 20, as may be well encountered.

The modification as shown in 4a eliminates either one of the first or second protruding bands 16, 18 while extending the other.

The modification as shown in 4e includes a modified shape to the main body portion and relocates the first and second protruding bands 16, 18 from an end of the main body portion to a more central portion thereof.

The modifications as shown in 4c and 4d teach that it is possible to eliminate the first and second protruding bands 16, 18 entirely by increasing the overall size of the main body portion. Variation of the shape of the main body portion is also taught as shown in each of the illustrations (4a-4e).

A concave tip portion 42 is shown as including a recessed area that is provided at a top of each of the devices (4a-4e). During use, the concave tip portion 42 is disposed on a side of the finger 20 proximate the nail 22. The concave tip portion 42 can also be included with the preferred version of the blood-draw finger restraint 10, as was described hereinabove.

A purpose of the concave tip portion 42 is to encourage flexing of the main body portion around the finger 20 (around the longitudinal axis 14). An additional purpose is to ensure that a sufficient uncovered area of the tip of the finger 20 that is disposed under the nail 22 remains exposed for creating the necessary puncture 34.

All of the possible alternate device shapes are adapted to be placed around the finger 20 and all help to prevent bending of the finger 20 after lancing. Also, all of the possible alternate device shapes provide optimum control of the finger 20 by the lab technician and allow for the application of increased pressure to opposite sides of the alternate device to express an additional quantity of the blood 12 for use with the test strip 36 (or other test device). Also, all of the alternate device shapes are economical to manufacture and disposable after use.

The blood-draw finger restraint 10 also provides an additional important benefit. After the blood-draw procedure is complete, the blood-draw finger restraint 10 is used to maintain the finger 20 in an erect or extended position, as shown in FIG. 3, while a bandage (also known as a band-aid, not shown) is applied over the puncture 34.

When the blood-draw procedure is complete, the lab technician easily slips the blood-draw finger restraint 10 off of the finger 20 by urging it toward the nail 22 and continuing to urge it in that direction until it is off the finger 20.

The time that is saved by use of the blood-draw finger restraint 10 allows for each lab technician to serve more people in a given period of time. This reduces the number of lab technicians, medical assistants or nurses (i.e. medical staff or phlebotomists) that are required by the lab which generally helps to lower the cost of drawing blood.

Also very important, the entire blood-draw procedure is accomplished by the one lab-technician. Help is not required, thereby greatly reducing the labor costs involved. Also, the labor cost of having to repeat failed attempts and the material costs (such as lancets) associated with repeated attempts are also eliminated.

The blood-draw finger restraint 10 simplifies the drawing of blood, especially from children. Accordingly, less skilled lab technicians are required. This also saves additional money for the lab.

Whenever the lab technician (or other medical staff person that is drawing the blood 12) releases the finger 20, the child will automatically and instinctively bend the finger 20 in the direction shown by arrow 28. Accordingly, the blood-draw finger restraint 10 is also used to maintain control of the finger 20 until after the bandage has been applied. At that time the portion of the blood-draw procedure that requires interaction with the child is complete.

The invention has been shown, described, and illustrated in substantial detail with reference to the presently preferred embodiment. It will be understood by those skilled in this art that other and further changes and modifications may be made without departing from the spirit and scope of the invention which is defined by the claims appended hereto.

What is claimed is:

1. A blood-draw finger restraint for drawing blood from a finger of a hand of a person, comprising:

(a) a body portion that is formed of flexible sheet of material, and including at least one member that is attached to said body portion, and wherein said body portion and said at least one member are formed of a contiguous and continuous piece of said flexible sheet material, and wherein said body portion and said member each include a preset tendency to curve around a common longitudinal axis thereof in a circle sufficient to form a generally cylindrical shape with a longitudinal opening therein; and wherein when a force is applied to said member and to said body portion that is sufficient to urge and maintain said member and said body portion in an open position that does not include said cylindrical shape, said member and said body portion are able to be placed proximate said finger and in a position wherein said preset tendency to curve supplies a force that is attempting to urge said body portion and said member toward and around said finger, and wherein when said force is removed from said member and said body portion while said member and said body portion are disposed proximate said finger, said preset tendency of said member and said body portion supplies a force that is sufficient to urge said member and said body portion into said cylindrical shape and around said finger until said finger is disposed in an interior of said cylindrical shape and a portion of said member and a portion of said body portion are in contact with an exterior of said finger, and wherein said member and said body portion include a combined overall length that is greater than a circumference of said finger, and wherein when said finger is disposed in said interior of said cylindrical shape a fingertip of said finger is not covered and is accessible;

(b) means for limiting an amount said finger can bend around an axis of a joint of said finger, and wherein said joint is disposed closer to a fingernail of said finger than any other remaining joint of said finger when said blood-draw finger restraint is disposed in said cylindrical shape and around said finger, and wherein when said blood-draw finger restraint is disposed in said cylindrical shape around said finger said portion of said combined overall length of said member and said body portion that is greater than said circumference of said finger includes an area of overlap that extends over a portion of said blood-draw finger restraint, and wherein when said blood-draw finger restraint is disposed around said finger said body portion and said member and said area of overlap of said flexible sheet material combine together to provide sufficient rigidity for limiting an amount that said joint of said finger can be bent by said person, and wherein said area of overlap does not include any fastening means, and wherein said preset tendency to curve around said longitudinal axis supplies a force to said body portion and to said at least one member that attempts to increase the size of said area of overlap, and wherein said preset tendency to curve automatically adjusts to a size of said finger when said finger includes a smaller circumference, and wherein when said finger includes a larger circumference said preset tendency to curve around said longitudinal axis supplies a force to said body portion and to said at least one member that decreases said area of overlap and thereby automatically adjusts to said size of said finger that includes said larger circumference;

wherein said blood-draw finger restraint, when disposed proximate said finger and in a position suitable for use, does not extend beyond said finger or make contact with a palm of said hand, and wherein said blood-draw finger restraint does not pass around or otherwise cooperatively engage with a remaining finger of said hand other than with said finger, and wherein a tip of said finger is not covered by any portion of said blood-draw finger restraint and wherein said tip of said finger includes a sufficient uncovered and unobstructed area to permit a lancing of said tip of said finger sufficient to produce a puncture in said tip of said finger;

wherein a splint is not attached to or used with said blood-draw finger restraint;

wherein a panel that is detachably-attachable with respect to said blood-draw finger restraint is not attached to or used with said blood-draw finger restraint; and wherein said blood-draw finger restraint does not include any additional fastening means for securing said blood-draw finger restraint proximate said finger other than said preset tendency of said body portion and said member to curve around said longitudinal axis.

2. The blood-draw finger restraint of claim 1 wherein said means for limiting an amount said finger can bend around an axis includes a portion of said body portion that is disposed under said joint when said blood-draw finger restraint is disposed around said finger.

3. The blood-draw finger restraint of claim 2 wherein said body portion includes an ornamental shape that is affixed thereto.

4. The blood-draw finger restraint of claim 1 wherein said blood-draw finger restraint includes a second member, and wherein a combined length of said body portion and said member and said second member is sufficient to extend fully around said circumference of said finger and to include said area of overlap.

5. The blood-draw finger restraint of claim 1 wherein said flexible sheet material includes a plastic.

6. The blood-draw finger restraint of claim 1 wherein said flexible sheet material includes a plastic sheet.

7. The blood-draw finger restraint of claim 6 wherein said plastic sheet includes said preset tendency to curve around said longitudinal axis thereof in a circle.

8. The blood-draw finger restraint of claim 1 wherein said blood-draw finger restraint is provided in a sterile condition.

* * * * *